(12) United States Patent
Martineau et al.

(10) Patent No.: US 8,979,911 B2
(45) Date of Patent: Mar. 17, 2015

(54) POROUS BONE SCREW

(75) Inventors: Paul A. Martineau, Westmount (CA); Louis-Philippe Lefebvre, Boucherville (CA); Edward J. Harvey, Westmount (CA)

(73) Assignees: The Royal Institution for the Advancement of Learning/McGill University, Montreal, Quebec (CA); National Research Council of Canada, Ottawa, Ontario (CA)

( * ) Notice: Subject to any disclaimer, the term of this patent is extended or adjusted under 35 U.S.C. 154(b) by 400 days.

(21) Appl. No.: 13/501,581

(22) PCT Filed: Oct. 13, 2010

(86) PCT No.: PCT/CA2010/001645
§ 371 (c)(1),
(2), (4) Date: Jun. 29, 2012

(87) PCT Pub. No.: WO2011/044697
PCT Pub. Date: Apr. 21, 2011

(65) Prior Publication Data
US 2012/0271362 A1 Oct. 25, 2012

Related U.S. Application Data

(60) Provisional application No. 61/251,085, filed on Oct. 13, 2009.

(51) Int. Cl.
*A61B 17/04* (2006.01)
*A61B 17/86* (2006.01)
*A61F 2/08* (2006.01)
*B22F 3/11* (2006.01)
*A61B 17/56* (2006.01)

(52) U.S. Cl.
CPC .............. *A61B 17/863* (2013.01); *A61B 17/864* (2013.01); *A61B 17/866* (2013.01); *A61B 2017/561* (2013.01)
USPC ............................................... 606/304; 419/2

(58) Field of Classification Search
USPC .................. 606/76, 300, 301, 304, 321, 331; 428/550; 419/2; 470/8–10
See application file for complete search history.

(56) References Cited

U.S. PATENT DOCUMENTS

| | | | |
|---|---|---|---|
| 4,950,270 A | 8/1990 | Bowman et al. | |
| 5,360,448 A | 11/1994 | Thramann | |
| 6,660,224 B2 | 12/2003 | Lefebvre et al. | |
| 8,475,505 B2 * | 7/2013 | Nebosky et al. | 606/304 |
| 2008/0269893 A1 | 10/2008 | Bhatnagar et al. | |

* cited by examiner

*Primary Examiner* — Andrew Yang
*Assistant Examiner* — Diana S Jones
(74) *Attorney, Agent, or Firm* — Sand & Sebolt

(57) ABSTRACT

A bone screw is described which includes a one-piece threaded screw body composed at least partially of a rigid foam. The screw body is headless and includes a bore extending therethrough to define a cannula and thereby providing the screw body with an annular shape defining a radial wall thickness. At least a central portion of the screw body is formed of the rigid foam which defines a matrix having a plurality of inter-connected pores therein. The inter-connected pores are disposed throughout the complete radial wall thickness of the screw body from an outer surface of the screw body to an inner surface thereof within the cannula, such as to permit bone in-growth through the complete radial wall thickness of the annular screw body. The inter-connected pores and the cannula thereby respectively allow bone in-growth through the complete radial wall thickness and the full axial length of the screw body.

22 Claims, 6 Drawing Sheets ately locate the screw in a desired location straddling the fracture site within the bone. In general, a compression screw allows the fractured bone to increase in strength and favours prompt healing, while decreasing the risk of non-union.
POROUS BONE SCREW

CROSS REFERENCE TO RELATED APPLICATIONS

This application is a National Stage Entry of PCT Application Serial No. PCT/CA2010/001645 having an international application date of Oct. 13, 2010, which application claims priority from U.S. Provisional Application Ser. No. 61/251,085, filed Oct. 13, 2009; the disclosures of which are incorporated herein by reference.

TECHNICAL FIELD

The present disclosure relates generally to the field of bone screws, and more particularly to screws used for bone fixation.

BACKGROUND

Compression bone screws are commonly used to join together, under compression, fractured fragments of a broken bone, and are inserted during a surgical intervention to precisely locate the screw in a desired location straddling the fracture site within the bone. In general, a compression screw allows the fractured bone to increase in strength and favours prompt healing, while decreasing the risk of non-union.

The scaphoid bone, located in the wrist generally between the radius and thumb, is the mechanical link between the proximal and distal carpal rows, is one of the most commonly fractured bone in the upper extremity. Wrist fractures often involve the scaphoid bone, and primarily occur due to axial compression with the wrist in extension, inducing a flexion moment on the scaphoid and causing a fracture. As a result of the flexion moment applied, as well as its relative small size and its location, displacement and/or deformity of the scaphoid is common. In addition, the scaphoid has a limited blood supply, and thus can become avascular after a fracture, which may lead to bone necrosis.

Consequently, it is often necessary to surgically intervene to treat a fracture of the scaphoid. Such surgical intervention typically involves the insertion of a compression bone screw in the scaphoid. Although un-displaced fractures have a high rate of healing when the wrist and thumb are immobilized for a prolonged period of time, there has nonetheless been a growing trend toward surgical intervention for fixation of acute un-displaced fractures (i.e. bone fractures wherein cracks in the bone may radiate in several directions but the bone fragments do not separate) of the scaphoid. However, most scaphoid fractures are displaced, and surgical intervention is clearly warranted in these cases. Surgical intervention and rigid internal fixation have shown to decrease time of healing and risks of non-union. Surgical intervention requires precise positioning of the implant or fracture fixation structure along the central axis of the scaphoid and spanning the fracture site, rigid fixation under compression and limited disturbance of the biology of the fracture site.

Due to the small size of the scaphoid bone (typically about 22 to about 30 mm in length), many challenges exist for designing and manufacturing bone screws suitable for use in the fixation of the scaphoid. Currently, compression screws used in scaphoid fixation have been designed to be left in place permanently, buried under articular cartilage and improvements have been made to the screw to increase compression. A commonly employed scaphoid fixation screw includes screw threads on opposed ends of the screw, each having a different pitch, such as to hold the portions of the scaphoid on opposite sides of the fracture site in compressive engagement with each other.

However, accurate placement of the screw and minimization of the space occupied by the screw such as to increase healing potential, are examples of areas where improvement is sought. Particularly when used for fracture fixation of very small bones such as the scaphoid, existing bone screws have been found to occupy valuable space where bone cannot re-grow and therefore the actual amount of bone available for healing of the fracture is often not optimized.

Accordingly, there remains a need for an improved screw for fracture fixation of bones, particularly but not necessarily small bones such as the scaphoid, which will permit both accurate placement of the screw within the bone and which optimizes the amount of bone available for healing of the fracture.

SUMMARY

Accordingly, there is provided an improved screw for bone fracture fixation.

In a very general aspect, the screw for bone fracture fixation may comprise a headless compression screw that is cannulated to allow for accurate placement within the bone and which is composed at least partially of a porous foam material that defines a plurality of inter-connected pores which permit bone in-growth through the complete cross-section of the porous screw portion, thereby minimizing the space occupied by the metallic screw within the fractured bone.

In one particular aspect of the present invention, there is provided a bone screw comprising a one-piece screw body comprised at least partially of a rigid foam and having at least one external thread thereon, the screw body being headless, a bore extending through an axial length of the screw body to define a cannula and providing the screw body with an annular shape having a radial wall thickness, at least a central portion of the screw body being formed of said rigid foam which defines a matrix defining a plurality of inter-connected pores therein having a size of about 30 to about 500 microns, the inter-connected pores being disposed throughout the complete radial wall thickness of the screw body from an outer surface of the screw body to an inner surface thereof within the cannula such as to permit bone in-growth through the complete radial wall thickness of the annular screw body, the inter-connected pores and the cannula thereby respectively allowing bone in-growth through the complete radial wall thickness and the axial length of the screw body.

There is also provided, in accordance with another particular aspect of the present invention, a method of producing a bone screw comprising forming a one-piece headless screw body out of a rigid metallic foam that is entirely porous throughout and defines a plurality of inter-connected pores having a size of about 30 to about 500 microns in diameter, including providing at least one thread on an external surface of the screw body, and forming a bore extending through an entire axial length of the screw body, the bore forming a cannula that defines an annular radial wall thickness of the screw body, and disposing the inter-connected pores throughout the radial wall thickness of the screw body such as to allow for bone in-growth through the full radial wall thickness and into the cannula.

There is further provided, in accordance with another particular aspect of the present invention, a compression bone screw for fixation of the scaphoid comprising a leading end, a headless trailing end and at least one external thread therebetween, a bore extending an axial length of the screw between the leading and trailing ends, the bore being radially centered to define an annular screw body having a radial wall thickness, and the screw being formed in one-piece by a porous metallic foam, the porous metallic foam defining a plurality of inter-connected pores therein which are substantially free of material until bone in-growth through the pores occurs, the plurality of inter-connected pores being disposed through the complete radial wall thickness of the bone screw, said bone in-growth being permitted radially through the complete radial wall thickness and axially through the bore.

DESCRIPTION OF THE DRAWINGS

Reference is now made to the accompanying drawings, showing by way of illustration a preferred embodiment thereof, and in which.

DETAILED DESCRIPTION

Figure 1:
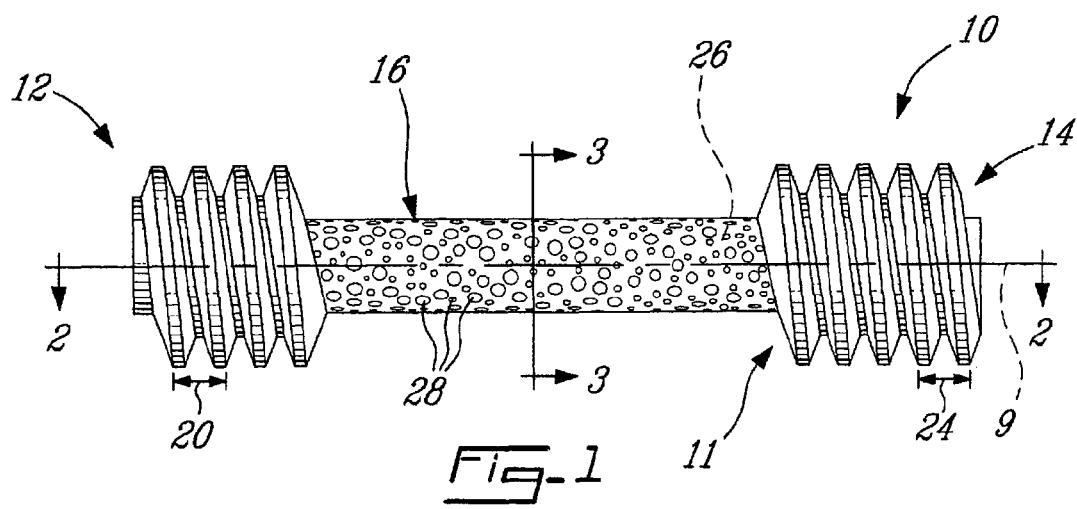
FIG. 1 is a top plan view of one embodiment of a compression bone screw, having a porous central portion.

The bone screws described herein are intended principally for use in joining together fractured fragments of a broken bone. Although the bone screw described herein may be particularly well suited for use in the fixation of the scaphoid bone in the wrist, it may also be adapted for the fixation of other bones, for example wherein compression across the fracture site is desirable in order to help the healing process. Additionally, although the present bone screws will be principally described with respect to their use as compression screws, it is to be understood that the present bone screws may also comprise non-compression screws, for example screws which apply tension in a bone, and/or which may be used for applications other than fracture fixation. For example, the presently described bone screws may also be employed to fasten external fixators in place to a bone, or to fasten other medical implants in place, such as rods used to stabilize the vertebral column for example.

All embodiments of the compression bone screw described herein are however at least partially porous, particularly in at least a region which is adapted to bridge the fracture line itself in the case of fracture fixation screws. As will be seen, the present bone screws may also be entirely composed of a porous material, such that the compression screw is porous throughout. By being porous through the complete thickness, or cross-sectional area, of at least the central body portion of the screw, the space occupied by the screw inside the bone is thereby limited in that the porous nature of the screw is less dense than a fully solid screw would be, thereby increasing the area available for the bone to grow into and through the screw. Accordingly, the interconnected pores defined within the foam material which forms the present bone screws extend throughout the entirety of the screw, or at least a portion thereof, thereby allowing for bone growth through at least the full radial cross-section of the screw such that the bone can gain access to the central cannula bore and subsequently grow inside the central portion of the screw. This permits the bone to fully grow through, in, and around the screw. Such a fully porous bone screw thus acts much like a scaffold or skeleton through which bone can grow, resulting in an improved healing of a fractured bone that is fixed using the present bone screws.

Accordingly, the presently described bone screws help to improve bone healing rates such as to offer a better potential for patient recovery. Other advantages of the present bone screw may also exist, such as lower probabilities of arthritis development or losing motion into the hand/wrist due to bone necrosis or failure of the fractured bone parts to fuse together. The present bone screw possesses a strength and torsional rigidity adequate to resist its surgical insertion into the bone and its removal when necessary. Given the very small nature of bone screws adapted for use in scaphoid fracture fixation and the porous nature of the present bone screw, ensuring sufficient strength and torsional rigidity is important. The bone screws described herein also have adequate flexibility/stiffness permitting it to resist flexion moment, thus increasing the strength of a fractured bone that is fixed together by the screw.

Figure 2:
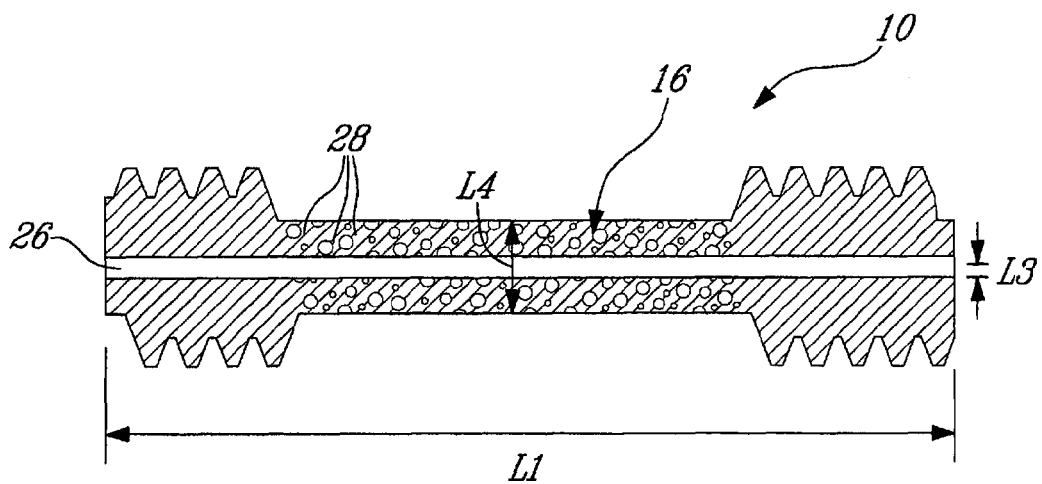
FIG. 2 is a longitudinal cross-sectional view of the compression bone screw of FIG. 1, taken through line 2-2 in FIG. 1.
Figure 3:
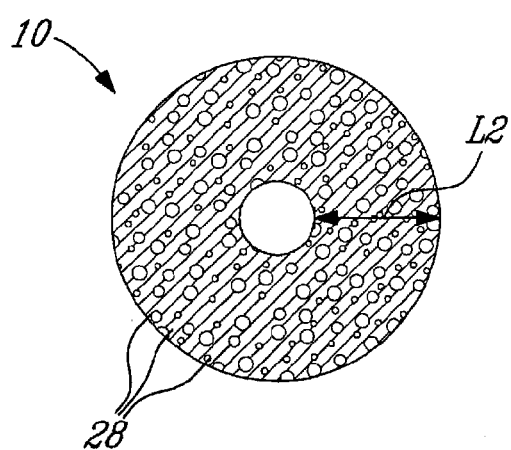
FIG. 3 is a cross-sectional view of the compression bone screw of FIG. 1, taken through line 3-3 in FIG. 1.

Referring now to FIGS. 1 to 3, which illustrate a headless bone screw 10 composed of an integrally formed, one-piece body 11 having a first threaded extremity 12 and an opposed second threaded extremity 14 spaced apart by a central portion 16. Although in this embodiment of the bone screw 10 this central portion 16 is un-threaded, as will be seen below the central portion of the bone screw may also be threaded, for example such that the first extremity, central portion and second extremity form a continuous external thread on the screw body. The screw body 11 may, in at least one particular embodiment, be one-piece or monolithic (i.e. integrally formed from a single piece of material), however the properties of this monolithic body may not necessarily be uniform throughout. The body 11 generally defines an elongated shape having a longitudinal axis 9 extending through the center thereof. The screw body 11 may be substantially symmetrical to a transverse plane that is perpendicular to the longitudinal axis 9, as seen in FIG. 3 for example wherein the central portion 16 of the body defines an annular circular profile. However, it is to be understood that this may only be strictly true for the central portion 16, when it is not threaded. For example, if the two threaded extremities have different pitches (as seen in FIG. 5 for example) the screw body will not be symmetric to such a transverse plane.

In this particular embodiment, the first threaded extremity 12 has a first pitch 20 and the second threaded extremity 14 has a second pitch 24. While it is to be understood that for a compression screw, these pitches must be different in order to create the compression force between the two bone portions respectively fastened by the first and second extremities, the first and second pitches 20, 24 may also, however, be the same. This may be true, for example, in an embodiment wherein the bone screw is not a compression screw. Additionally, it is to be understood that the first and second threaded extremities as defined herein need not necessary be separate threaded portions but may be merely the leading and trailing portions of a continuously threaded screw.

Figure 5:
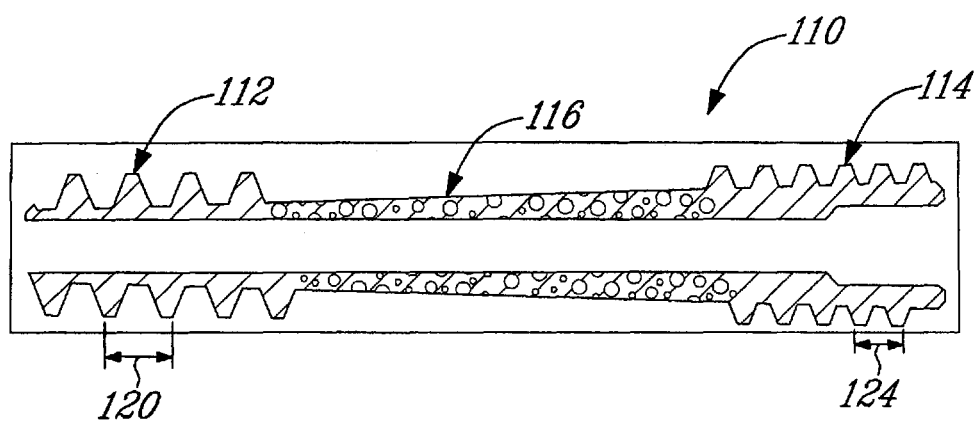
FIG. 5 is a longitudinal cross-sectional view of another embodiment of a compression bone screw, having opposed extremities with different thread pitches and a porous central portion.

This difference in screw pitch between the two ends of the screw is better seen in FIG. 5 with reference to the bone screw 110, which includes at least a fully porous central body portion 116 extending between the first and second threaded extremities 112, 114, wherein the first threaded extremity 112 that has a pitch 120 that is greater than the pitch 124 of the second threaded extremity 114. For example, the pitch 120 of the leading screw thread 112 may be preferably selected to be greater than the pitch 124 of the trailing screw thread 114, which generates a compressive force between the two portions of the fractured bone respectively engaged with the leading and trailing screw threads 112 and 114.

A centrally disposed and longitudinally extending bore 26 extends throughout the axial length L1 of the body 11, as seen in FIG. 2, thereby forming a longitudinally extending cannula through the body 11 of the compression screw 10. As such, the screw 10 is said to be cannulated. The cannulation of the screw 10 allows for increased ease and precision of insertion, and generally permits a less invasive surgical approach. For example, a guide wire which is received within the longitudinal bore 26 may be used to guide the screw 10 into a precise location in the bone. The longitudinal cannula bore 26 therefore has a diameter L3 which is suitable for receiving such a guide wire therethrough, in order to optimize the ease and precision of insertion of the screw. The guide wire may have, for example, a 1 mm to 1.5 mm diameter, and therefore the diameter L3 of the cannula 26 is, in at least this embodiment, sized just slightly greater than the 1 mm-1.5 mm guide wire to be snugly received therein.

As best seen in FIG. 3, the cannula 26 may also be radially centered within the body 11 such as to define a radial thickness L2 which, in an exemplary embodiment, is substantially constant along at least the length of the central portion 16 of the body 11. This radial thickness L2 is in effect the thickness of the annular wall defined by the cannula bore 26 within the central screw body portion 16. This radial wall thickness L2 may be relatively thin, for example approximately 1 to 1.5 mm for example, which improves bone in growth through the entire wall thickness and therefore through the entire central portion 16 of the screw body 11. In the present embodiment, at least the entire central body portion 16 is completely porous, in that the pores which are defined in the central body portion extend through the complete radial wall thickness L2. This differs, for example, from a mere porous surface coating that may be applied to an otherwise solid screw surface.

In the embodiment shown in FIGS. 1-3, the central portion 16 of the screw body 11 is unthreaded, thereby defining the first and second threaded extremities 12, 14.

Figure 6:
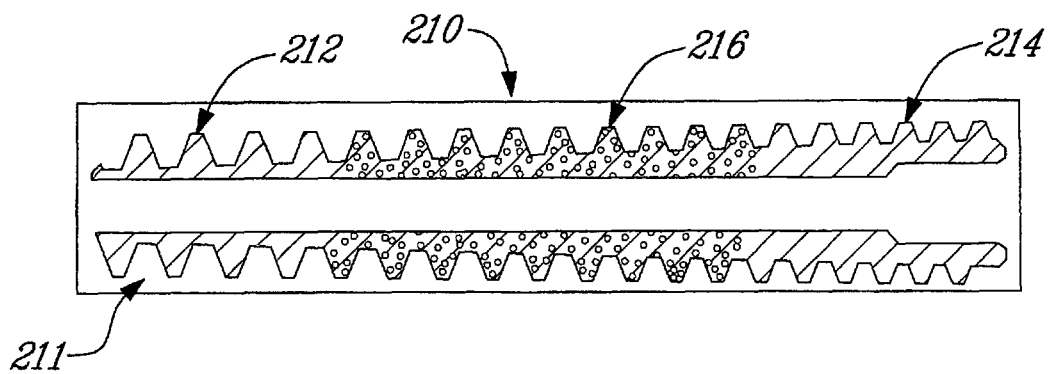
FIG. 6 is a longitudinal cross-sectional view of another embodiment of a compression bone screw, being threaded along its complete length with a variable pitch and having a porous central section.

However, in the embodiment shown in FIG. 6, the compression bone screw may alternately be formed with threads extending the complete longitudinal length of the entire screw 210, thereby providing a continuously threaded screw body 211. This configuration, i.e. having an external thread extending along the full axial length of the screw, may be preferred for some applications and may also be more efficiently manufactured. In this embodiment, the central portion 216 of the screw 210 is threaded in addition to the threaded extremities 212 and 214, or rather, the screw thread extends un-interrupted from the leading end to the trailing end of the screw. As such, the threaded extremities are merely the leading and trailing portions of the full-length screw thread. The pitch of the first and second extremities 212 and 214 may be different, and in fact the continuously threaded body 211 may have a continuously variable pitch throughout the axial (i.e. longitudinal) length of the screw 210, as is the case for the screw 210 depicted in FIG. 6, in which the pitch gradually decreases from the leading end 212 to the trailing end 214 of the screw 210, or in other words the threads are more spaced apart at the leading end 212 and more densely spaced at the trailing end 214.

The threaded central body portion 216 may be formed of the same material and/or having the same properties as the central portion 16 described in further detail below, and is therefore formed of a porous material that defines pores throughout a complete thickness of the material. As will be described in further detail, this porous material may be a porous foam, and preferably may be a metallic foam for example made of titanium, stainless steel, tantalum, magnesium, ceramic, or a combination and/or alloy of any thereof. The threads themselves in this porous, threaded central portion 216 are therefore also made of this porous material. Such a fully threaded compression screw 210, with at least the central portion 216 thereof being completely porous, may allow for more compression at the fracture site. In addition, cutting leading threads may also be provided on the leading tip (the left-hand threaded portion 212 in FIG. 6) may also be provided and can improve and simply ease of insertion of the screw.

Referring back to the bone screw 10 of FIGS. 1-3, at least the central portion 16 of the bone screw 10 is formed having pores 28 throughout the complete radial thickness L2 of the body 11, to allow for bone in growth through the full radial thickness L2 (and therefore the full radial—or transverse—cross-sectional area) of the screw. As opposed to simply being a surface treatment, the fully porous nature of the material used to form at least the central portion 16 of the screw 10 is such that the pores 28 are inter-connected and disposed throughout the entire radial thickness L2 and throughout the entire longitudinal length of at least the central portion 16 of the screw body 11. Therefore, the porous nature of the material of the compression screws described and depicted herein is such that it differs substantially from an overall more dense material (ex: solid metal) that simply has holes formed therein. In other words, forming a plurality of holes or perforations (formed by drilling, for example) in a dense material does not make it porous throughout, as per the definition of "porous" as used herein and as produced by the metallic foam structure of the present porous screws. The pores 28 described herein interconnect to form a plurality of interconnected voids, each in communication with the next adjacent void, and which extend substantially uniformly in all directions of the given porous section of the screw, and at least in the radial direction from the outer surface of the screw to the inner cannula bore thereof. This allows for improvements both in terms of greater bone in growth (and through-growth) into the compression screw and improved means of manufacturability. It is important that the pores 28 be hollow, i.e. voids, which are not pre-filled or otherwise obstructed with other material, as the hollow pores 28 must be clear voids in order to permit ready bone in growth through the entire bone screw. Accordingly, the interconnected pores defined within the foam material which form the bone screw extend throughout the entirety of the screw, or at least the porous portion thereof, thereby allowing for bone growth through at least the full radial cross-section of the screw such that the bone can gain access to the central cannula bore and subsequently grow inside the central portion of the screw. This permits the bone to fully grow through, in, and around the screw.

In at least one particular embodiment, the pores 28 within the central portion 16 are substantially uniformly sized and substantially uniformly spaced apart, as much as is reasonably feasible based on the production process used to form the bone screw. The material selected to form at least the central portion 16, or alternately the entire screw 10 as will be described further below, has a porosity which is such that these bone-in growth pores 28 are defined throughout the entire thickness of bone screw.

However, it is to be understood that the pores of the rigid foam material which makes up the compression bone screws described herein do not necessarily need to be of equal size or equally, or homogenously, spaced apart. The rigid foam, which is preferably but not necessarily composed of a metallic foam, may be comprised of a porous sintered metal made from metal powders using powder metallurgy techniques for example. This metallic foam material forms a metal matrix or network that defines inter-connected pores throughout. This interconnected porosity allows fluid flow from one side of the screw body to the other, and therefore allows for full bone in growth (in fact permits bone through-growth). This is in contrast, for example, with isolated surface pores (ex: machined or otherwise formed in a solid metallic part), which do not have connectivity between each other and with both surfaces of the component.

As discussed above, the pores 28 minimize the space occupied by the screw, thereby increasing the amount of bone which is able to grow through the bone screw 10. This is particularly useful when the bone screw is employed in an already small bone, such as the scaphoid for example. The fully porous nature of the screw 210, or the fully porous nature of at least the central body portion 16 of the bone screw 10, allows for the space occupied by the screw within the bone to be also available for healing by permitting new bone in growth through the structure of the fracture-fixating bone screw 10, thereby effectively minimizing the volume within the bone element that is occupied by the metallic material of the screw and thus potentially increasing healing potential.

As noted in further detail below, following insertion of the bone screw 10, a material may also be injected into the cannula 26 within the screw in order to impregnate the pores of the screw from the inner cannula outward. This material may include, for example, a bone growth promoting resin or bone protein, or a structurally reinforcing cement, etc.

Although the porous material selected to form at least the central portion 16 of the bone screw 10 may be any suitable material having the pores 28 defined throughout an entire thickness thereof, in one embodiment this porous material is a metallic foam, made for example of a titanium alloy. Although other ranges are of course possible, the pores 28 have a size (ex: diameter), in at least one particular embodiment, of about 30 to about 500 microns (i.e. μm), but preferably between 50 to 400 μm, to achieve desired levels of bone in growth and mechanical strength, and the porous material has a porosity ranging from 30% to 80%, but preferably between 40 to 70% to obtain a desired level of mechanical strength.

In one exemplary embodiment, at least the central portion 16, but preferably the entire screw (see FIGS. 4 and 7 and related description), is composed of a biocompatible and rigid metallic foam that may preferably be, but is not necessarily, non-ferromagnetic and thus allows magnetic resonance imaging (MRI) of the bone. However, it is to be understood that a ferromagnetic metal may also be used. Examples of possible metals which may be used to form the metallic foam from which the present screws are formed include titanium, tantalum, stainless steel, TiNi, etc. Even though the material of the screw may not be magnetic per se, it is also to be understood that this non-ferromagnetic material might be composed of constituents which themselves are at least partially ferromagnetic (ex: stainless steel contains iron and nickel which are themselves ferromagnetic even if the resultant metal is not).

In order to achieve a fully porous structure for the present bone screw, it has been found particularly advantageous to form the screw from a metallic foam material. Such a foam is produced having pores of a selected size range throughout its entire structure, and formed into the desired screw shape. The metallic foam may contain titanium, magnesium, iron, tantalum or an alloy thereof such as stainless steel, Ti6Al4V or a ceramic. Although a number of methods may be used to produce such an open cell metallic foam which forms the present bone screws, in one particular embodiment the method used is as described in U.S. Pat. No. 6,660,224 which issued Dec. 9, 2003, the entire contents of which is incorporated herein by reference. Generally, a dry powder mixture containing an organic solid binder, inorganic particles and a foaming agent is heated and foamed while the organic binder is melted. The solid foamed structure is heated to eliminate the organic binder and then the remaining inorganic three-dimensional network structure is sintered into a porous rigid structure.

The configuration of the bone screw 10 as well and the specific material selected are such that the screw 10 has adequate stiffness to resist flexion moment on the scaphoid bone, as well as sufficient torsional rigidity to permit screw insertion. While the present bone screw may be made of a titanium, magnesium, tantalum, iron based alloys or ceramics, or any combination thereof, other ferromagnetic or non-ferromagnetic alloys may also be used, however preferably non-ferromagnetic alloys are used such as to allow for postoperative MRI to proceed without interference.

Referring now back to the bone screw 10 shown in FIG. 2, the cannula 26 having a diameter L3 traverses the entire axial (i.e. longitudinal) length L1 of the compression screw 10. In one embodiment, the diameter L3 of the cannula bore 26 in the screw 10 may be about 1 mm to about 1.4 mm, in order to optimize the ease and precision of the insertion. The cannula allows for tool engagement and increased ease of insertion of the bone screw 10. Studies point to the fact that accurate placement of the bone screw 10 within the scaphoid may be a more important variable than the amount of compression generated by the bone screw at the fracture site. Therefore, a high precision is required to install the screw and the cannula 26 permits a less invasive surgical approach. If the removal of the screw is necessary because of various medical reasons, for example infection, the screw may be removed by using the cannula 26 and a cannulated drill.

As noted above, in one particular application of the present porous bone compression screw 10 is used for fracture fixation of the scaphoid. In this embodiment, the outer diameter L4 of the central portion 16 of the screw body 11 may be 3 or 4 mm, and the axial length L1 of the entire screw 10 may be from 16 to 30 mm, for example produced in a number of different possible sizes within this range (ex: 16, 18, 20, 22, 24, 26, 28 and 30 mm). The length of the compression screw used for fixation would depend on the anatomical variation of the fractured bone. The relative sizes of L1, L2 and L4 may also be varied and selected as required, and will depend on the orthopaedic application of the compression screw.

Figure 4:
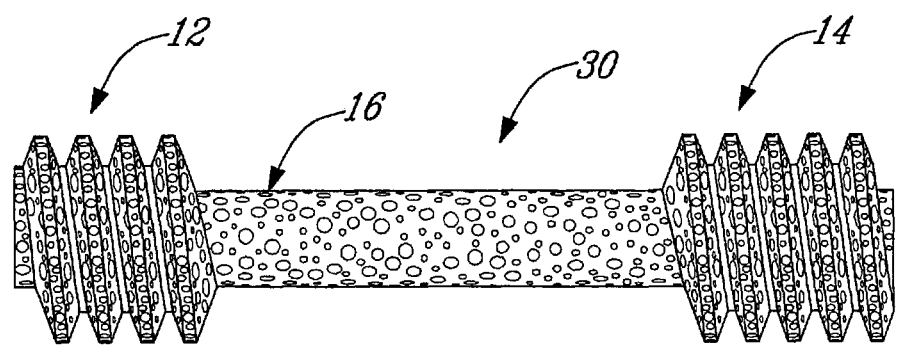
FIG. 4 is a top plan view of another embodiment of a compression bone screw, being porous throughout.

FIG. 4 shows an alternate compression screw 30 which is similar in all respects to the bone screw 10 described above, however rather than having only a porous central portion, the entire headless compression screw 30 is formed of a porous material and therefore the screw 30 is porous throughout its complete length and width. Accordingly, the entire body 31 of the bone screw 30 is made of a single piece porous material and therefore both the threaded extremities as well as the un-threaded central portion are fully porous throughout. The compression screw 30 may thus be made of a single, unitary material having substantially homogeneous properties throughout.

Figure 7:
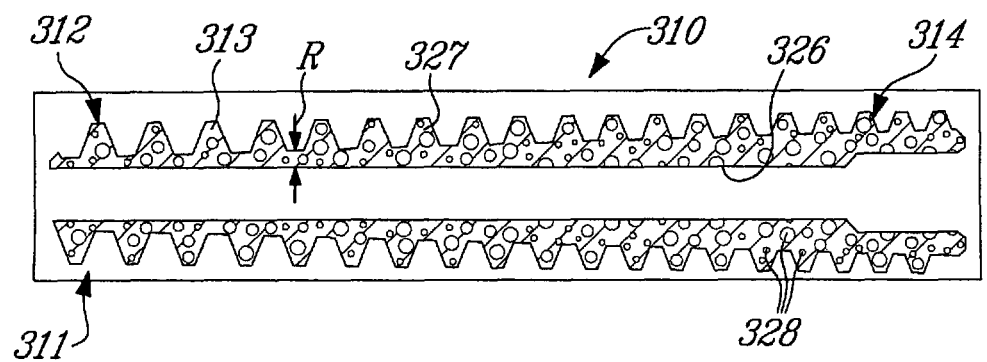
FIG. 7 is a longitudinal cross-sectional view of another embodiment of a compression bone screw that is threaded along its complete length and that is porous throughout.

Referring to FIG. 7, the compression bone screw 310 is similar to the screw 210 shown in FIG. 6 in that it has a continuous external thread 313 along its entire axial length and has a continuously variable pitch along the full axial length of the screw, wherein the pitch of the thread 313 at the leading end 312 of the screw is greater than the pitch of the screw thread 313 at the trailing end 314 of the screw. Additionally, the radial thickness R of the screw wall 327 increases gradually from the leading end 312 to the trailing end 314 of the screw 310, and as such the radial length of each thread is greatest at the leading end 312 and smallest at the trailing end 314, as can be readily seen in FIG. 7, as well as in FIG. 6. The compression screw 310 of FIG. 7 is completely formed of the porous, rigid foam material as per the screw 30 of FIG. 4 described above. In other words, the entire threaded body 311 of the screw 310 is made of the same fully porous foam material and thus has pores 328, similar to those described above, through the complete axial length and complete radial width (and thus complete transverse or radial cross-sectional area) of the screw body 311. As such, the compression bone screw 310 has a screw body 311 which defines a continuous external thread 313 having a variable pitch and which thread extends along the full axial length of the screw body. Additionally, the entire screw 110, including the complete screw body and the external threads themselves, is composed of a porous metallic foam material that forms a matrix defining a plurality of inter-connected pores therein that are disposed throughout the complete radial wall thickness of the screw body (and therefore completely through the full cross-sectional area of the screw body) such as to provide bone-growth communication between the external surface of the screw comprising the threads and the inner bore or cannula 326 extending through the center of the screw body 311.

In comparison with a fully solid metal screw of the prior art, the present fully porous bone screws, such as the bone compression bone screw 310 of FIG. 7 and the compression bone screw 410 as will be described below, have been found to reduce the total volume occupied by the screw within the bone by more than 50%, which accordingly allows for significantly greater bone growth across the fracture line and thus improved healing speed and post-fracture strength. Further, in tests conducted in a fractured scaphoid, the cross-sectional area occupied by the central portion of the present porous compression bone screws was found to be only 15% of the fracture area, whereas this amount is often as much as 35% of the fracture area occupied by solid bone screws of the prior art. This results in increased bone area remaining, allowing for improved healing, when the screw is in place.

Referring now to FIGS. 8A to 8B and 9A to 9C, a compression screw 410 in accordance with another preferred embodiment is depicted. The compression screw 410 is similar to the screw 310 of FIG. 7, in that the entirely of the body 411 of the screw 410 is threaded, a single and continuous external thread 413 having a continuously variable pitch extends along the full axial length of the screw body 411. The entire screw 410 is composed of a rigid metallic foam that is entirely porous throughout, in that the interconnected pores 428 are disposed throughout the complete axial length and the complete radial thickness of the screw body 411 (and thus through the complete transverse annularly-shaped cross-section of the screw body), such that the plurality of interconnected pores 428 provide a bone-growth communication between an outer surface 437 of the screw body 411 and an inner surface 439 thereof within the cannula bore 426 axially-extending through the center of the screw body. Accordingly, the interconnected pores 428 formed by the rigid (preferably metallic) foam material extend throughout the entirety of the complete screw 410, thereby allowing for bone growth through the full radial cross-section of the screw such that the bone can gain access to the central cannula bore 426 and subsequently grow inside the central portion of the screw 410. This permits the bone to fully grow through, in and around the screw 410. The fully porous bone screw 410 thus acts much like a scaffold or skeleton through which bone can grow, resulting in an improved healing of a fractured bone that is fixed using the present bone screws.

Figure 8A:
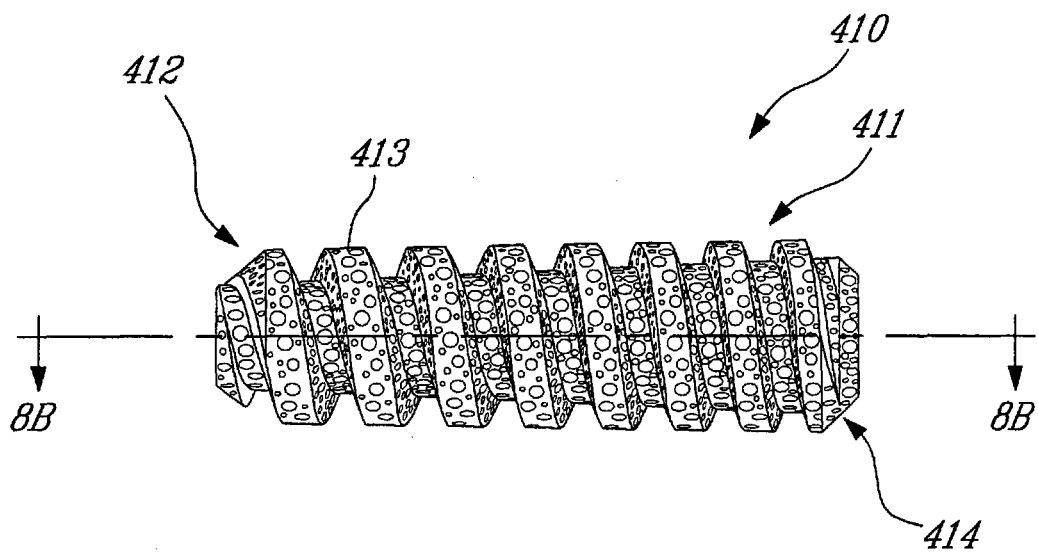
FIG. 8A is a top plan view of another embodiment of a compression bone screw that is porous throughout.
Figure 8B:
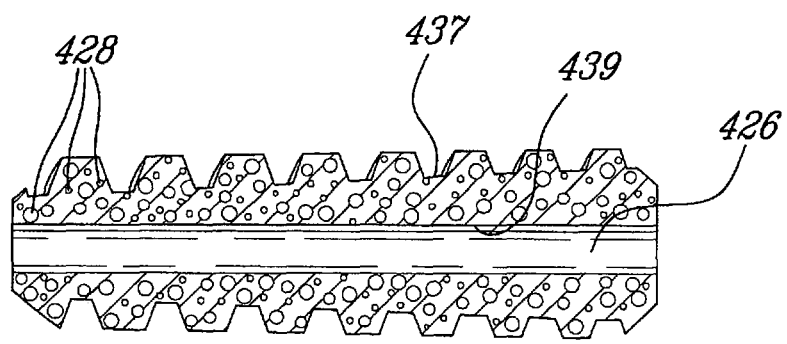
FIG. 8B is a longitudinal cross-sectional view of the compression bone screw of FIG. 8A, taken through line 8B-8B in FIG. 8A.

As can be seen, the pitch of the continuous external screw thread 413 varies continuously and gradually along the full axial length of the threaded body 411, from a greater pitch at the leading end 412 of the screw to a smaller pitch at the trailing end 414 thereof. As seen in FIG. 8B, the screw 410 includes a constant diameter cannula bore 426 extending longitudinally through the complete length of the screw body. The screw 410 is preferably integrally formed as a monolithic, one-piece, structure that is entirely porous throughout, as noted above.

Figure 9A:
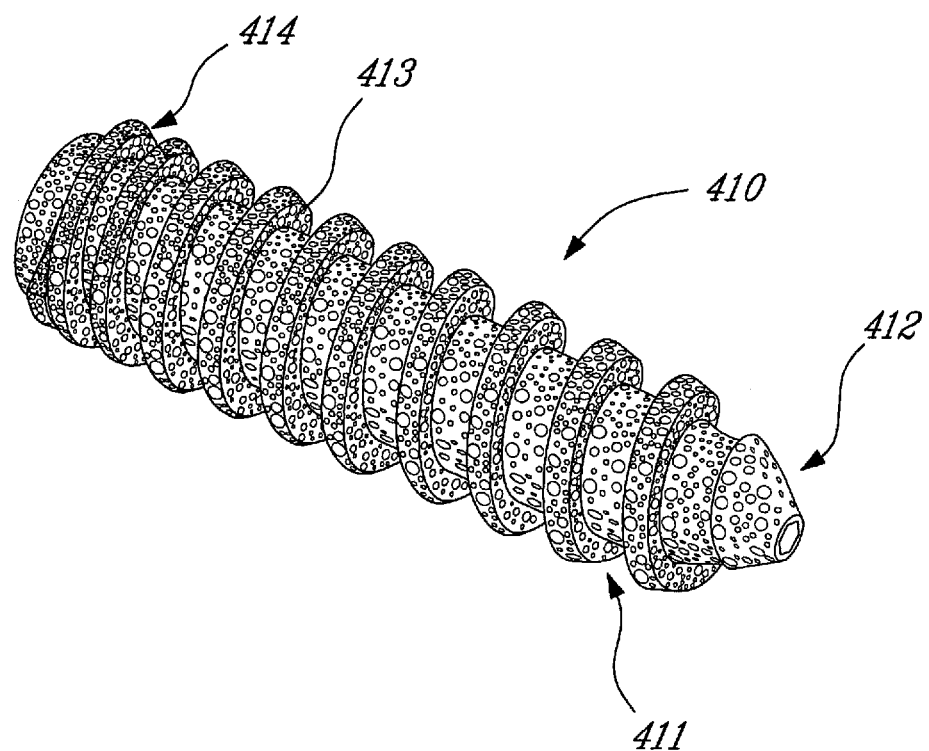
FIG. 9A is a perspective view of an example of the compression bone screw of FIGS. 8A-8B, and is entirely composed of a porous metallic material.
Figure 9B:
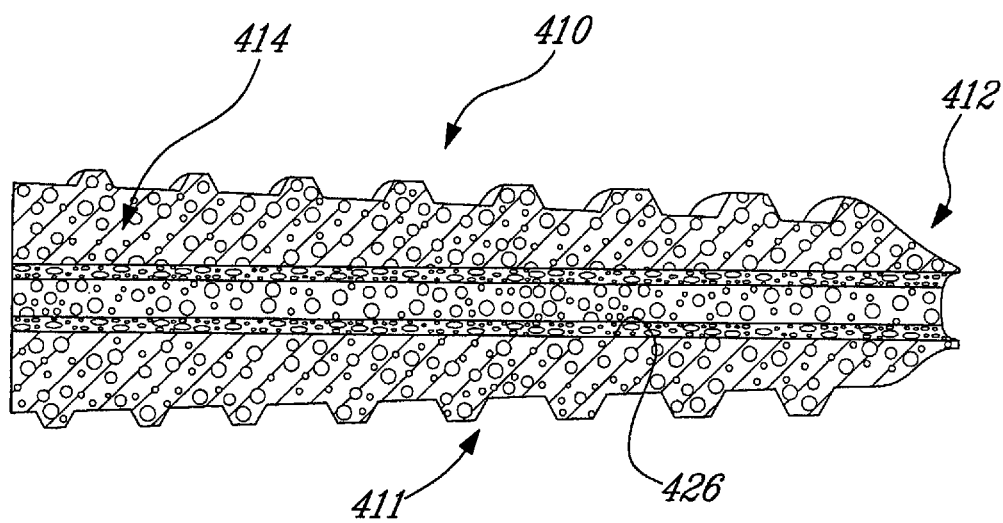
FIG. 9B is a longitudinal cross-sectional view of the compression bone screw of FIG. 9A.
Figure 9C:
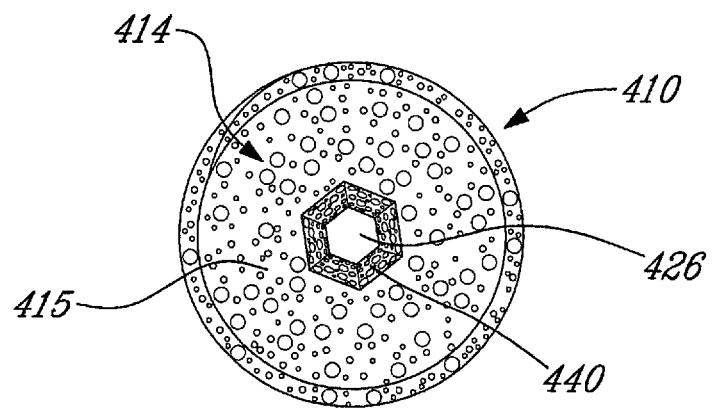
FIG. 9C is an end view of the compression bone screw of FIG. 9A.

FIGS. 9A to 9C depict an example of the compression bone screw 410 as described above. The compression bone screw 410 is entirely formed, in one-piece, by a metallic foam material that is entirely porous throughout. The externally threaded body 411 of the bone screw 410 has a continuous thread 413 along its complete axial length (i.e. from leading end 412 to trailing end 414 of the screw) with a pitch that gradually and continuously decreases from the leading end 512 to the trailing end 514 thereof. As seen in FIG. 9B, the longitudinally extending cannula 526 through the center of the screw body 411 is substantially constant in diameter along the axial length of the screw, thereby defining a continuously increasing radial wall thickness from the leading to the trailing end of the screw. As best seen in FIG. 9C, the trailing end 414 includes a hexagonal shaped opening 440 in the flat end 415 of the screw which communicates with the cannula 426 of the screw body. This hexagonal shaped opening 440 provides a mounting point for receiving a driving device, such as a screwdriver, that can be used to rotatably drive the screw during the insertion thereof into the bone.

Although the compression bone screw 410 may be formed such as to have substantially constant properties throughout, it is to be understood that the manufacturing process used to create the metallic foam screw 410 may result in slight non-homogeneities in the screw. However, in an alternate configuration, the screw 410 may also be provided with intentionally differing properties in different regions thereof. For example, the central portion of the screw, which is most likely to extend across the actual fracture line in the bone, may be provided with more pores or a more porous structure (i.e. less dense) than the opposed ends. It is to be understood, however, that the annular walls of the screw body must nonetheless maintain a minimum torsional strength such as to permit the screw to be rotationally driven into, and out of when necessary, the bone.

A coating may also be applied onto any one of the above-described the bone screws in order to assist and/or enhance the bone in growth therethrough. This coating may be, for example, hydroxyapatite (HA) or another suitable biocompatible bone growth promoting material. Additionally, the bone screws may be coated with a pharmaceutical product to help ease healing of the bone following surgery. Such a bone-growth promoting product or a pharmaceutically active product which eases healing of a bone fracture may also be inserted directly into the bone screws, as described in further detail below.

The cannula of any of the bone screws described herein may further contain, in another alternate embodiment, a material introduced therein which may help induce bone growth. This may include, for example, a bone protein. This bone-growth promoting product may be easer "pre-loaded" into the cannula of the bone screw prior to its insertion into the bone, or may alternately be injected into the cannula once the screw is in place within the bone. Further still, a plug or rod may be introduced into the cannula bore 26, either before or after insertion of the screw in place within the bone, in order to increase the structural integrity of the screw 10 or in order to further assist with bone in growth through the entire diameter of the screw (or at least the central portion 16 thereof). For example, a plug or narrow rod of titanium foam can be inserted down into the cannula bore 26 in the bone screw 10. This permits the cannula 26 to be used in order to permit an accurate insertion of the bone screw, and then the cannula 26 can be filled with a porous foam rod which in effect renders the entire cross-section of the screw body porous in nature. In yet another alternate embodiment, the cannula bore 26 may be filled with a bone cement or another hardenable material which acts to reinforce the screw 10 and improve the fixation of the bone fracture.

It is to be understood that the material(s) chosen for the presently described compression bone screws is such that they are fully biocompatible and suitable for use in connection with fracture fixation within humans and animals.

The term "rigid" as used herein with reference to the foam material from which the present compression screws are formed is understood to mean structurally self-supporting and being sufficient strong (ex: has sufficient torsional stiffness) to withstand insertion into (and removal from) a bone element using an appropriate driving device (ex: screwdriver, powered or manual) without bending or substantially deflecting or compressing, etc.

The above description is meant to be exemplary only, and one skilled in the art will recognize that changes may be made to the embodiments described without departing from the scope of the invention disclosed.

For example, the outer diameter of the bone screw may be non-constant through the length of the bone screw, and therefore the radial side wall thickness and/or the depth of the outer threads may vary over the length of the screw. While the inner cannula bore diameter may preferably be substantially constant, this too may vary along a length of the screw. Additionally, although the entire central portion of the bone screw is described as being made of the defined porous material, it is to be understood that less that the entire length of this central portion may be porous. For example, only a predetermined portion, likely that which will overlap the fracture site, of the central body portion (whether threaded or note) may be made porous while the remainder of the central portion and in fact a remainder of the entire screw may be a solid material (i.e. substantially free of pores). Still other modifications which fall within the scope of the present invention will be apparent to those skilled in the art, in light of a review of this disclosure, and such modifications are intended to fall within the appended claims.

What is claimed:

1. A bone screw comprising a one-piece screw body comprised at least partially of a rigid foam and having at least one external thread thereon, the screw body being headless, a bore extending through an axial length of the screw body to define a cannula and providing the screw body with an annular shape having a radial wall thickness, at least a central portion of the screw body being formed of said rigid foam which defines a matrix defining a plurality of inter-connected pores therein having a size of about 30 to about 500 microns, the inter-connected pores being disposed throughout the complete radial wall thickness of the screw body from an outer surface of the screw body to an inner surface thereof within the cannula such as to permit bone in-growth through the complete radial wall thickness of the annular screw body, the inter-connected pores and the cannula thereby respectively allowing bone in-growth through the complete radial wall thickness and the axial length of the screw body.

2. The bone screw as defined in claim 1, wherein the bone screw is composed entirely of the rigid foam and defines said plurality of inter-connected pores through the entire screw body.

3. The bone screw as defined in claim 1, wherein the rigid foam is a porous sintered metal made from metal powders using powder metallurgy, the rigid metallic foam forming a metal matrix defining the pores throughout.

4. The bone screw as defined in claim 3, wherein the rigid metallic foam comprises at least one of titanium, tantalum, magnesium, iron or an alloy of any one or more thereof.

5. The bone screw as defined in claim 1, wherein the bone screw is a compression screw and the screw body includes at least a threaded leading end and a treaded trailing end, the threaded leading end having a pitch greater than that of the trailing end.

6. The bone screw as defined in claim 5, wherein the screw body includes a central portion between the threaded leading end and the treaded trailing end, the central portion being threaded such that the central portion, the leading and trailing ends form a continuously threaded screw body.

7. The bone screw as defined in claim 6, wherein the pitch of the continuously threaded screw body varies gradually along the axial length of the continuously threaded screw body.

8. The bone screw as defined in claim 1, wherein at least the porous portion of the screw body has an external coating thereon, the coating including at least one of a bone growth promoting material, a pharmaceutical healing agent and a structurally reinforcing cement.

9. The bone screw as defined in claim 1, wherein the cannula includes at least one of a bone growth promoting material, a pharmaceutical healing agent and a structurally reinforcing cement therein.

10. The bone screw as defined in claim 1, wherein the bone screw is a scaphoid fracture fixation screw, the axial length of the screw body being from about 10 to about 30 mm, the central portion having an external diameter of about 3 to about 4 mm, and the cannula having a diameter from about 1.0 mm to about 1.4 mm.

11. The bone screw as defined in claim 1, wherein the size of said pores is about 50 to about 400 microns.

12. The bone screw as defined in claim 1, wherein the foam is a non-ferromagnetic metallic foam.

13. The bone screw as defined in claim 1, wherein the radial wall thickness of the annular screw body increases from a leading end to a trailing end of the screw.

14. Use of the bone screw as defined in claim 1 for fracture fixation of the scaphoid.

15. A compression bone screw for fixation of the scaphoid comprising a leading end, a headless trailing end and at least one external thread therebetween, a bore extending an axial length of the screw between the leading and trailing ends, the bore being radially centered to define an annular screw body having a radial wall thickness, and the screw being formed in one-piece by a porous metallic foam, the porous metallic foam defining a plurality of inter-connected pores therein which are substantially free of material until bone in-growth through the pores occurs, the plurality of inter-connected pores being disposed through the complete radial wall thickness of the bone screw, said bone in-growth being permitted radially through the complete radial wall thickness and axially through the bore.

16. The compression bone screw as defined in claim 15, wherein the bone screw is composed entirely of the porous metallic foam and said plurality of inter-connected pores are disposed throughout the entire bone screw.

17. The compression bone screw as defined in claim 15, wherein the porous metallic foam comprises at least one of titanium, magnesium, tantalum, iron or an alloy of any one or more thereof.

18. The compression bone screw as defined in claim 15, wherein the porous metallic foam is a porous sintered metal made from metal powders using powder metallurgy.

19. The compression bone screw as defined in claim 15, wherein the radial wall thickness of the annular screw body increases from the leading end to the trailing end of the screw.

20. The compression bone screw as defined in claim 15, wherein each of the plurality of pores has a size between about 30 and about 500 microns.

21. The compression bone screw as defined in claim 20, wherein the size of said pores is about 50 to about 400 microns.

22. The compression bone screw as defined in claim 15, wherein at least one of an outer surface of the screw body and the cannula has a coating thereon which includes one or more of a bone growth promoting material, a pharmaceutical healing agent and a structurally reinforcing cement.

* * * * *